US012551331B2

(12) United States Patent
Long et al.

(10) Patent No.: US 12,551,331 B2
(45) Date of Patent: Feb. 17, 2026

(54) DIVERSIFIED GRAFTS HAVING HETEROGENOUS FEATURES AND METHODS FOR MAKING AND USING SAME

(71) Applicant: Musculoskeletal Transplant Foundation, Edison, NJ (US)

(72) Inventors: Marc Long, Monmouth Junction, NJ (US); Evangelia Chnari, Scotch Plains, NJ (US); Jeffrey Cartmell, Freehold, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 731 days.

(21) Appl. No.: 17/893,467

(22) Filed: Aug. 23, 2022

(65) Prior Publication Data

US 2023/0068127 A1 Mar. 2, 2023

Related U.S. Application Data

(60) Provisional application No. 63/236,956, filed on Aug. 25, 2021.

(51) Int. Cl.
*A61F 2/12* (2006.01)

(52) U.S. Cl.
CPC ...................................... *A61F 2/12* (2013.01)

(58) Field of Classification Search
CPC ................ A61F 2/12; A61F 2002/0068; A61F 2210/0057; A61F 2220/0008;
(Continued)

(56) References Cited

U.S. PATENT DOCUMENTS 5,403,347 A 4/1995 Roby et al.
10,765,507 B2 9/2020 Moses
(Continued)

FOREIGN PATENT DOCUMENTS

EP 3085337 10/2016
EP 3628272 4/2020
(Continued)

OTHER PUBLICATIONS

Sigalove S., et al., "Evaluation of the safety of a galaflex-alloderm construct in prepectoral breast reconstruction", Plastic and Reconstructive Surgery, 2022, vol. 150, pp. 75-81.
(Continued)

*Primary Examiner* — Suzette J Gherbi
(74) *Attorney, Agent, or Firm* — Cole Schotz, P.C.; Marcella M. Bodner, Esq.

(57) ABSTRACT

Diversified grafts suitable for use in repair and reconstruction procedures are provided. Some diversified grafts comprise two or more heterogenous features which form regions having different preferred properties. A diversified graft useful for pre-pectoral breast reconstruction, meshing is provided on an upper pole of the diversified graft and a plurality of slits arranged in particular patterns is provided on a lower pole of the graft, whereby the upper pole has a greater expansion ability and the lower pole has lesser degree of expansion ability but maintains greater load bearing capacity which is necessary to support the lower pole of the breast undergoing reconstruction, while allowing for fluid egress. In other embodiments, the diversified graft comprises two or more components which are combined by attaching them to each other to form a larger graft of the required size. The components may be smaller pieces of the same material or different materials.

18 Claims, 3 Drawing Sheets

(58) Field of Classification Search
CPC ...... A61F 2230/0008; A61F 2250/0014; A61F 2250/0018; A61F 2/0063; A61L 27/3604; A61L 27/50; A61L 2430/04
See application file for complete search history.

(56) References Cited

U.S. PATENT DOCUMENTS

| | | | | |
|---|---|---|---|---|
| 11,439,490 | B2 | 9/2022 | Felix | |
| 11,439,498 | B2 | 9/2022 | Doucet et al. | |
| 2008/0086216 | A1 | 4/2008 | Wilson | |
| 2008/0097601 | A1 | 4/2008 | Codori-Hurff | |
| 2009/0082864 | A1 | 3/2009 | Chen | |
| 2009/0240342 | A1 | 9/2009 | LIndh | |
| 2010/0047309 | A1* | 2/2010 | Lu | A61L 27/446 623/13.14 |
| 2012/0004723 | A1* | 1/2012 | Mortarino | A61F 2/12 623/8 |
| 2012/0221105 | A1 | 8/2012 | Altman | |
| 2014/0188250 | A1* | 7/2014 | Fearnot | A61L 27/60 623/23.72 |
| 2020/0360129 | A1 | 11/2020 | Moses et al. | |
| 2024/0277467 | A1 | 8/2024 | Parker et al. | |

FOREIGN PATENT DOCUMENTS

| | | |
|---|---|---|
| WO | 2017066568 | 4/2017 |
| WO | 2023028030 | 3/2023 |

OTHER PUBLICATIONS

International Patent Application No. PCT/US2022/041166, filed on Aug. 23, 2022.
Written Opinion of the International Searching Authority issued on Dec. 22, 2022 for International Patent Application No. PCT/US2022/041166.
International Search Report issued on Dec. 22, 2022 for International Patent Application No. PCT/US2022/041166.

* cited by examiner

DIVERSIFIED GRAFTS HAVING HETEROGENOUS FEATURES AND METHODS FOR MAKING AND USING SAME

CROSS-REFERENCE TO RELATED APPLICATIONS

The present application claims the benefit of U.S. Provisional Application No. 63/236,956, filed on Aug. 25, 2021, the entire disclosure of which is hereby incorporated by reference herein.

FIELD

The present invention relates generally to diversified grafts suitable for use in medical surgical repair and reconstruction procedures. The present invention also relates to methods for making and using such diversified grafts. More particularly, the present invention relates to diversified grafts comprising two or more heterogenous features which form regions of varied physical properties on the diversified grafts.

BACKGROUND

Several types of surgical repair and reconstruction procedures are performed to treat a body feature or condition thereof, in whole or in part, of a patient. Such procedures may be performed for any number of reasons including repairing or reconstructing a body feature which has been injured or otherwise damaged by disease or by trauma, which may be accidental, incidental, intentional, or combinations thereof. Other reasons include, modifying, altering, or restoring, the health, shape, functionality, etc., of a body feature, for medical reasons, cosmetic reasons, or both.

Some surgical repair and reconstruction procedures require, or benefit from, the use of one or more grafts which are implanted in, on, or adjacent to, the body feature of a patient undergoing treatment. Grafts suitable for such uses may be produced, in whole or in part, from tissue derived matrices (i.e., tissue samples recovered from one or more donors and processed by physical processes, chemical treatments, or combinations thereof), as well as from other naturally derived or synthetic materials, and combinations thereof.

Several issues are presented when producing and using such grafts in surgical repair and reconstruction procedures. For instance, without limitation, the available sizes and cost of tissue derived matrices used for producing the grafts may present limitations to their use. Additionally, without limitation, the issue of whether the graft possesses the combination of physical properties and characteristics which are beneficial or required depending on the body part undergoing treatment and the particular surgical repair or reconstruction procedure being performed.

Applicant has developed diversified grafts which address and even resolve several issues which arise when grafts are used during repair and reconstruction procedures, by including heterogenous features in each diversified graft that address varied requirements presented by a body feature undergoing treatment, a particular procedure being performed, or both.

BRIEF DESCRIPTION OF THE FIGURES

The present invention will be further explained with reference to the attached drawings, wherein like structures are referred to by like numerals and/or letters throughout the several views. The drawings shown are not necessarily to scale, with emphasis instead generally being placed upon illustrating the principles of the presently described and contemplated invention.

DETAILED DESCRIPTION

Figure 1:
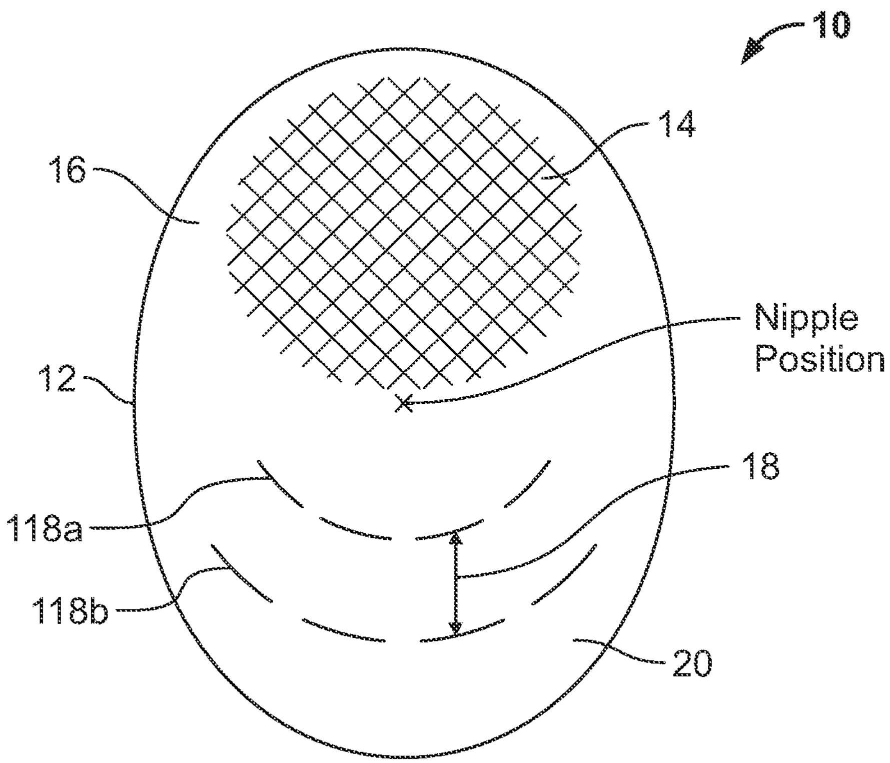
FIG. 1 is an exemplary embodiment of a diversified graft which includes meshing and a plurality of slits arranged in patterns that form regions having different properties.

Detailed embodiments of the present invention are disclosed herein. It should be understood that the disclosed embodiments are merely illustrative of the invention which may be embodied in various forms. In addition, each of the examples given in connection with the various embodiments of the invention is intended to be illustrative, and not restrictive. Further, unless otherwise indicated, the figures are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as examples for teaching one skilled in the art to variously employ the present invention.

The following definitions are provided for clarification and enhancing understanding of the following description, but are not intended to be limiting.

The term "biocompatible," as used here, means that a graft or implant, when implanted in a subject, does not cause one or more adverse effects such as, without limitation, toxicity, injury, foreign body reaction or rejection, irritation, allergic or other histamine reaction, disruption of cellular structure or function, etc.

As used herein, the term "condition" refers to a variety of healthy and unhealthy states of a living subject and its organs, tissues, and biological systems, and includes both normal, healthy and functioning states, as well as abnormal, unhealthy, damaged, and malfunctioning states, whether caused by a disorder, disease, infection, injury, trauma, or other mechanism or event.

The term "contacting" and "implanting" and their various grammatical forms, are used interchangeably and refer to a state or condition of touching or of immediate or local proximity, internally or externally, such as positioning or implanting a composition, graft, or implant in, on, or proximate to, a body feature to be treated. Contacting a composition to a target destination, such as a body feature or an implant site, may occur by any means of administration known to persons of ordinary skill in the relevant art.

The terms "derived," "derived from," and "produced from" and all their grammatical forms, are used herein interchangeably to mean that the material or composition being described is produced by subjecting one or more specified starting materials to one or more process steps or techniques, which may be physical, chemical, or combinations of physical and chemical techniques, as are appropriate depending on the starting material and intended material or composition product. For example, without limitation, a "tissue derived matrix" is a composition which has been produced by subjecting a selected tissue sample to one or more process steps or techniques, which may be physical, chemical, or combinations thereof. (e.g., recovering the tissue sample from a donor, cutting to size, disinfecting, decellularizing, and drying by lyophilizing). A component of a graft which is produced from a biocompatible synthetic polymer means that the component is produced by subjecting the selected biocompatible synthetic polymer to one or more process steps or techniques, which may be physical, chemical, or combinations thereof (e.g., optionally blending, combining, mixing, etc., the selected polymer with one or more additives such as rheology modifiers, emulsifiers, dispersing agents, stabilizers, etc., and shaping by thermoforming, extrusion, crosslinking, etc.).

As used herein, the term "donor" means a living or deceased mammal from which one or more tissues, organs, other body parts, or portions thereof, are recovered or harvested. Suitable mammalian donors include, but are not limited to: human, primate, bovine, porcine, equine, ovine, rodent, leporine, canine, feline, etc.

As used herein, the term "graft" means a biologically compatible material, tissue, or substance which is introduced into the body of a subject, either permanently or temporarily, to replace, improve or supplement the structure or function of tissue, an organ, or other body feature, of a subject or patient. A graft may be used for the administration or delivery of a therapeutic agent or substance. Grafts may be absorbed or integrated, in whole or in part, into a patient's body after implantation.

The term "implant," as used herein means a device or material that replaces a missing body feature or portion thereof, which may be lost or absent due to trauma, disease, congenital condition, or a combination there, and is intended to restore the normal function(s) and/or shape of the missing body part. Furthermore, an implant can be any material, device or substance which is introduced into the body of a subject, either permanently or temporarily, to replace, improve or supplement the structure or function of tissue, an organ, or other body feature of the subject and includes, but is not limited to, those used for the administration or delivery of a therapeutic agent or substance. A "prosthetic device" refers to a particular kind of implant and means a device, either external or internal, that substitutes for or supplements a missing or defective part of the body (i.e., body feature), or augments performance of a natural function of a body feature.

As used herein, the term "tissue derived matrix" means a material which is produced, by one or more processing steps and techniques, from one or more samples of tissue recovered from one or more donors. The one or more processing steps and techniques may be physical, chemical, and combinations thereof. The samples of tissue may be the same or different types of tissue as one another. Furthermore, it is possible for a single tissue sample to include more than one type of tissue when recovered, and may or may not be subjected to separation of the different types of tissue during processing. The donor of one or more of the tissue samples from which a tissue derived matrix is produced may be: the same individual as the recipient of a graft comprising the tissue derived matrix (i.e., autogenic), or a different individual of the same species as the recipient (i.e., allogenic), or a different species as the recipient (i.e., xenogenic).

The performance of, and results achieved by, many repair and reconstruction procedures would be improved or enhanced by providing and using a diversified graft which includes regions having different properties formed by heterogenous features, or multiple components, or both. Such a diversified graft would provide one or more advantages and benefits including, but not limited to:

(a) reduced consumption or use of expensive and/or scarce raw materials (e.g., tissue samples),
(b) reduced overall cost of the graft by more efficient combination of raw materials (e.g., tissue samples and other naturally derived and synthetic materials),
(c) greater versatility in a single graft possessing regions of different properties (i.e., differences in one or more of function, type, and degree) to address various requirements presented by some repair and reconstruction procedures, and
(d) combinations thereof.

To provide the aforesaid advantages and benefits, diversified grafts in accordance with the invention described and contemplated herein comprise a main body comprising a tissue derived matrix. The tissue derived matrix may be derived from one or more tissue samples recovered from one or more donors. The tissue samples may be one or more types of tissue including but not limited to: dermal, adipose, submucosal, fascia, other planar tissue types, and combinations thereof.

In some embodiments, the diversified grafts further comprise two or more heterogenous features which form two or more regions of the main body, each region having a property which is different from at least one other region. In other embodiments, the diversified grafts further comprise two or more components, which may be formed from the same type of material, or not, and are combined with one another to form the main body. In still other embodiments, the diversified grafts comprise two or more components which are combined with one another to form the main body, as well as two or more heterogenous features which form regions of the main body, each having different properties, wherein each region of the main body may be commensurate with a respective one of the two or more components or not. These general embodiments will be described in further detail below, after discussion of the contexts and requirements for such grafts generally presented by repair and reconstruction procedures.

Many surgical repair and reconstruction procedures for treating a body feature of a subject, or patient, involve implanting one or more grafts, implants, and prosthetic devices in, on, or adjacent the body feature to be treated. A portion of, or an entire, body feature, such as, without limitation, a breast, a buttock, a cheek, a calf, etc., may be in need of, or benefit from, treatment for any number of reasons. Sometimes such surgical procedures are performed to treat, e.g., repair or reconstruct, a body feature which has been injured, damaged, wasted or atrophied by disease or trauma, whether accidental, incidental, intentional, or a combination thereof. In other cases, such surgical treatment is performed to reconstruct a body feature to modify, alter, or restore, the health, shape, functionality, etc., of a body feature, whether for medical reasons, cosmetic reasons, or both. Some surgical procedures are performed for a combination of such reasons. The diversified grafts described and contemplated herein are useful in virtually all such procedures and particularly beneficial in many such procedures as will be explained hereinbelow.

One of more grafts may be used to support or augment the adjacent tissue or tissues to enable a specific procedure that would not be otherwise feasible with the usage of the tissue, or to increase the probability of success of the medical/surgical procedure. For example, without limitation, a prepectoral breast reconstruction procedure may have a low chance of success without including use of a supportive material to support an implant placed between the chest muscle and a skin flap. The one or more grafts may be used, i.e., implanted in, on, or adjacent to the body feature, to provide weight bearing support, coverage, or both, to the body feature being treated. The one or more grafts may also, or instead, provide weight bearing support, coverage, or both, for an implant or prosthetic device also being implanted during the surgical procedure to repair or reconstruct a body feature. Sometimes, the one or more grafts are intended to provide some combination of the foregoing purposes and benefits. Of course, as understood by persons of ordinary skill in the relevant art, these are not the only possible purposes or functions that may be served by grafts when used in such surgical procedures.

Several issues are presented when producing and using such grafts in surgical repair and reconstruction procedures. For instance, when tissue samples derived from one or more donors are used to make such grafts, the size and dimensions of the graft which can be produced are sometimes limited by the size and dimensions of the tissue samples recovered and available at any particular time. The cost of grafts produced from tissue samples from donors is often a significant concern and may even be prohibitive in some contexts for some patients. While sometimes more suitable or beneficial, tissue derived grafts tend to be more expensive than grafts made from synthetic materials. Reducing expenses for surgical repair and reconstruction procedures is a continual goal which may be directly addressed by reducing the cost of the materials used, including the cost of the grafts.

Additional considerations include the acceptable or required physical properties of a graft, such as flexibility, elasticity, tensile or mechanical strength, weight or load-bearing capacity, and tear resistance, to name a few. Physical properties of a graft may be, at least in part, determined by the physical properties of the materials used to produce the graft. For instance, physical properties may vary significantly between different types of tissue samples (e.g., dermis, adipose, submucosa, fascia, placenta (including amnion, chorion, and umbilical cord), and other generally planar tissue types), and sometimes also vary between different portions or regions of a single tissue sample.

The physical properties required for optimizing the results of different surgical repair and reconstruction procedures will often guide the selection of the material for the grafts to be used. Furthermore, some procedures present situations in which the physical properties that are acceptable or required for the graft to have may vary at different portions or regions of the body feature being treated. Sometimes the acceptable or required physical properties of the graft vary depending upon the nature, size, and purpose of the implant or prosthetic device which is also being used to treat the body feature.

Several embodiments of grafts suitable for use in surgical repair and reconstruction procedures and which address one or more of the aforementioned issues and considerations will now be described. Although detailed embodiments of the grafts described and contemplated are described below as comprising an acellular dermal matrix and being useful and beneficial in connection with pre-pectoral breast reconstruction procedures, they are not limited to grafts which necessarily include an acellular dermal matrix, nor are they limited to use in pre-pectoral breast reconstruction procedures, or even treatment of a breast. Rather, persons of ordinary skill will recognize that the grafts described and contemplated hereinabove may comprise other materials, including, but not limited to, one or more natural or synthetic materials, including tissue derived matrices other than acellular dermal matrices. Furthermore, persons of ordinary skill will readily recognize and understand that the grafts described and contemplated herein will be useful and beneficial for use in surgical repair and reconstruction procedures which treat body features other than breasts, such as, without limitation, buttocks, cheeks, calves, etc.

One surgical repair or reconstruction procedure, but by no means the only one, which routinely involves implanting a graft, is breast reconstruction and, more particularly, pre-pectoral breast reconstruction. It should be noted that, as mentioned above, while the presently described and contemplated grafts will now be described in detail in connection with their use in pre-pectoral breast reconstruction procedures, persons of ordinary skill in the relevant art will readily recognize and understand that such grafts will also be useful and beneficial in other similar or analogous procedures for repairing or reconstructing other body features.

Pre-pectoral breast reconstruction is a method of reconstructing a breast, often after mastectomy necessitated by malignancy in the breast, using a breast implant which is placed in front of the patient's chest muscles (pectoralis major), in the pre-pectoral plane, rather than underneath the chest muscle as was done in earlier conventional reconstruction procedures. Typical pre-pectoral breast reconstruction procedures involve forming a skin flap using the skin covering the breast undergoing reconstruction and implanting a graft, which is generally planar, or sheet shaped, underneath the skin flap and in front of the chest muscles, which is often followed by implanting a breast implant, which is then supported to some degree by the graft.

In a pre-pectoral breast reconstruction procedure, the graft is typically affixed, at or near its peripheral edge, to the chest muscle using sutures, staples, biocompatible adhesive, and the like, or combinations thereof, to form a pocket between the chest muscle and the graft that receives the breast implant therein. Generally, the breast implant provides mass and shape for the reconstructed breast, while the graft supplements the skin flap that may be compromised or limited in its function when a breast implant is to be used. Grafts which are generally planar (e.g., sheet-shaped) prior to implanting and assume or reconfigure into a more three-dimensional shape or construction after implanting to conform to the skin flap associated with the breast undergoing reconstructive treatment have been developed and found useful for pre-pectoral breast reconstruction procedures.

Furthermore, planar grafts which comprise (e.g., are produced from) a tissue derived matrix such as an acellular dermal matrix, have been found to be particularly suitable for use in pre-pectoral breast reconstruction procedures. However, an acellular dermal matrix of sufficient size and dimensions for use as the graft may or may not be available at the time a breast having larger size or dimensions (i.e., mass, circumference, length, width, greatest depth or greatest distance from the pre-pectoral muscle, etc.) is undergoing reconstruction. This will depend on the availability of a dermal tissue sample of sufficient size and dimensions from which the acellular dermal matrix may be produced and available commensurate in time with the breast reconstruction procedure. Additionally, it is noted that grafts produced from a tissue derived matrix, such as an acellular dermal matrix, tend to be more expensive relative to other grafts which are not tissue derived, but rather are produced from other natural or synthetic materials which are formable into generally planar configurations of suitable size and shape.

The natural configuration and function of a human breast are determined and affected by different regions of the breast which normally and naturally have different load-bearing support or capacity requirements. More particularly, when a patient is standing or sitting upright, the "upper pole" of the breast refers to the area of the breast that is located above a horizontal plane that passes through the nipple. Similarly, the area of the breast that is located below a horizontal plane that passes through the nipple is referred to the "lower pole" of the breast. A planar graft suitable for use in pre-pectoral breast reconstruction procedures will be sized and shaped to generally lie beneath and line both the upper and lower poles of the breast and, therefore, has upper pole and lower pole regions corresponding to those areas of the breast.

The ability of a graft to cover and conform to the shape of a breast undergoing reconstruction is important for both the upper and lower poles of the graft. Expansion features such as, without limitation, cuts, slots, slits, meshing, fenestrations, etc., which extend or pass through a portion of, or the entire, thickness of the graft may be provided on at least a portion of the graft. Such expansion features provide that region of the graft with the ability to expand (i.e., expansion ability) and cover a greater area of breast and/or breast implant, as well as to more closely conform to the shape of the breast and/or breast implant (i.e., shape conformity), than it otherwise could without such expansion features. This allows a planar graft with a size and configuration insufficient to provide the necessary coverage and shape conformation to expand and provide that required degree of coverage and shape conformity. Techniques suitable and effective to form such expansion features are generally known, not particularly limited, and include, without limitation, meshing and fenestration devices, cutting, slicing, slashing, die stamping or cutting, with or without a pattern guide device, and combinations thereof.

It is noted that, as has been recognized by persons of ordinary skill in the relevant art, different types of expansion features provide different degrees of expansion abilities and shape conformities, while also compromising or reducing the load bearing capacity, and sometimes also the suture retention capabilities, of those regions of the graft having the expansion features. For example, without limitation, meshing and fenestrations will compromise or reduce the load bearing capacity and suture retention capability of the region of a graft on which they are formed, than a plurality of either linear or curved slits which are more spaced apart than typical meshing and fenestrations. Furthermore, a plurality of curved slits which are arranged on a region of a graft in two or more concentric circular patterns tend to provide better shape conformation than other arrangements of slits.

It is important for a graft used for pre-pectoral breast reconstruction procedures to have physical properties sufficient to adequately and securely support the skin flap associated with breast reconstruction in general. Relatively speaking, there is a greater need for the lower pole region of the graft to have sufficient physical properties (e.g., properties which approximate the tensile strength, elasticity, stiffness, ductility, etc., of natural dermis or skin) to sufficiently support the skin flap region associated with the lower pole of the breast than for the upper pole of the graft to support skin flap region associated with the upper pole of the breast. Accordingly, while maintaining (i.e., avoiding reduction of) physical properties of the lower pole of the graft is possibly of equal or greater importance, on balance, than maximizing its expansion capacity, the opposite is true of the upper pole of the graft.

Furthermore, a graft which includes a lower pole comprising material having mechanical strength and/or integrity which provide sufficient physical properties to support the skin flap region associated with lower pole of a breast undergoing reconstruction, need not also include an upper pole which necessarily comprises the same material, or a material of the same mechanical strength and/or integrity, as the material of the upper pole. Rather, such a graft may instead include an upper pole comprising material having a lower, yet sufficient, mechanical strength and integrity, as compared to the material of the lower pole, that is capable of supporting the skin flap region of the upper pole of the breast undergoing reconstruction. The flexibility to select and use such a material for the upper pole of the graft (i.e., a material which has lower mechanical strength and/or integrity as the material of the lower pole) may also provide an opportunity to select a material for the upper pole of the graft that is also less costly, more abundant or readily available, or both. Thus, where a different material having lower mechanical strength, but also lower cost and/or more abundant may provide the opportunity to lower the overall cost of the graft, ensure availability of a suitable graft notwithstanding scarcity or greater expense of the material most suitable for producing the lower pole of the graft.

The diversified grafts of the invention described and contemplated herein address and resolve several of the foregoing issues presented when producing and selecting a graft for use in repair and reconstruction procedures. In some embodiments, the procedure is a pre-pectoral breast reconstruction procedure. Several embodiments described hereinbelow allow for easier or greater expansion of the diversified grafts, whereby less tissue sample is used to create grafts which provides similar coverage compared to similar but larger grafts, thus conserving (i.e., optimizing) the amount of graft material required. The use of multiple pieces of tissue samples, with or without additional components produced from synthetic materials, combined together would also improve tissue yield. The use of two or more components which are made of a first material, such as a tissue derived matrix, and a second material which is different from and either less costly, more readily available, synthetic, etc. as compared to the first material.

In an exemplary embodiment, a diversified graft suitable for implanting in, on, or proximate to, a body feature undergoing a repair or reconstruction procedure, comprises a main body having a generally planar shape prior to implanting, the main body comprising two or more heterogenous features, each of which forms a region of the main body having at least one property. The at least one property of each region differs from the at least one property of at least one other region in function, type, degree, or a combination thereof. During and after implanting in, on, or proximate to, the body feature, the diversified graft may reconfigure from the generally planar shape to a three-dimensional shape which conforms to the size, shape, or both, of the body feature or a portion thereof.

The two or more heterogenous features may comprise a first feature and a second feature which is different from the first feature, for example without limitation, in structure, size, quantity, type of material, orientation, degree, or a combination thereof. The first feature may be present on a first region of main body of the diversified graft and provide the first region with a first property, and the second feature may be present on a second region of the main body of the diversified graft and provide the second region with a second property, wherein the second property is different from the first property in function, type, degree, or a combination thereof.

In some embodiments, for example, the main body of the diversified graft may include a first component made of a first material, such as a generally sheet shaped tissue derived matrix, which forms a first region of the main body, and a second component made of a second material, such as a synthetic mesh sheet, which forms a second region of the main body, wherein the two or more heterogenous features comprise the first material and the second material. The first and second components of such embodiments may be joined or attached to one another along their edges (which may or may not overlap to some extent, as desired or necessary) to form the main body which then has a larger sheet shape than either the first or second component. By using different materials, the diversified graft is expected to cost less than a graft made entirely from one or more tissue derived matrices, and may have different physical properties as are suitable to the different requirements for the different first and second regions of the main body of the diversified graft. Alternatively, in some embodiments, the first and second materials may be different types of tissue derived matrices, or the first and second materials may be different types of synthetic materials, or any combination contemplated and desired by persons of ordinary skill in the relevant art, depending upon the nature and use of the diversified graft to be formed. Furthermore, it is contemplated that, in some embodiments, the main body of a diversified graft may comprise two components, such as any described above, where the components are arranged and attached to one another and are at least partially, or even completely, overlapping, to form a multi-layer diversified graft.

In some embodiments, the body feature is a breast undergoing a pre-pectoral reconstruction procedure, and the main body of the diversified graft comprises a tissue derived matrix having a generally planar shape prior to implanting and two or more expansion features, each of which is selected from: meshing, fenestrations, perforations, slits, and cuts, and wherein each expansion feature is different from at least one of the other expansion features in structure, size, quantity, orientation, degree, or a combination thereof. Each of the two or more expansion features forms a region of the main body having a property selected from expansion ability, shape conformity, mechanical strength, load bearing capacity, and combinations thereof.

In some embodiments, the two or more heterogenous features may comprise a first expansion feature and a second expansion feature which is different from the first expansion feature in structure and quantity. The first expansion feature may be present on a first region of main body of the diversified graft and provide the first region with a first property, and the second feature may be present on a second region of the main body of the diversified graft and provide the second region with a second property, wherein the second property is different from the first property in degree.

For example, with reference to FIG. 1, a diversified graft in accordance with the invention described and contemplated herein may be a diversified pre-pectoral graft 10 comprising a main body 12 which comprises an acellular dermal matrix having a generally planar shape (as shown in FIG. 1) prior to implanting and a thickness (not shown per se). The acellular dermal matrix is, generally, a matrix derived from a dermal tissue sample (which may be autogenic, allogenic or xenogenic), and may optionally, also include some underlying adipose tissue, either alone or in combination with one or more synthetic materials. It should be recognized that the tissue derived matrices may be derived from dermal matrices which include a deeper cut dermis sample, or include solely a single layer graft, or multi-layer grafts attached in their natural configurations (i.e., a layer cut through deeper dermis and adipose), or multi-layer grafts of single-layer grafts layered/attached to each other. Furthermore, suitable synthetic materials are not particularly limited and include any flexible biocompatible material such as, without limitation, vicryl, polypropylene, etc.

The main body 12 of the diversified pre-pectoral graft 10 further comprises a first expansion feature, i.e., meshing 14, which forms a first region, i.e., an upper pole 16, of the main body 12. The main body 12 of the diversified pre-pectoral graft 10 further comprises a second expansion feature, i.e., a plurality of slits 18 which form two or more aligned semicircular patterns, e.g., two semicircular patterns **18*a*, 18*b* as shown in FIG. 1. Although not shown in the figures, it should be understood that the plurality of slits 18 may, without limitation, form two or more linear, arcuate, or concentric circular patterns. Each slit of the plurality of slits 18 extends entirely through the thickness of the acellular dermal matrix of the main body 12. The plurality of slits 18 forms a second region, i.e., a lower pole 20, of the main body 12**.

In the exemplary embodiment of FIG. 1, the upper pole 16 of the main body 12 of the diversified pre-pectoral graft 10 has at least one property, such as a first load bearing capacity, while the lower pole 20 of the main body 12 has at least one property, such as a second load bearing capacity which is different in degree from, i.e., greater than, the first load bearing capacity of the upper pole 16. Additionally, the upper pole 16 of the main body 12 of the diversified pre-pectoral graft 10 may have another property, such as a first expansion ability, while the lower pole 20 of the main body 12 also has another, such as a second expansion ability which is different in degree from, i.e., less than, the first expansion ability of the upper pole 16. Under the foregoing conditions, the (second) load bearing capacity of the lower pole 20 remains sufficient to provide the degree of support required by the lower pole of the breast undergoing reconstruction (not shown per se), while the upper pole 16 would advantageously be able to expand (e.g., increase its width, length, or both) to a greater degree than the lower pole 20, thereby providing increased coverage by the upper pole 16 when the diversified pre-pectoral graft 10 is implanted in the breast undergoing a pre-pectoral reconstruction procedure (not shown per se) and concurrently decreasing the overall amount of acellular dermal matrix required to make the diversified pre-pectoral graft 10.

Figure 2:
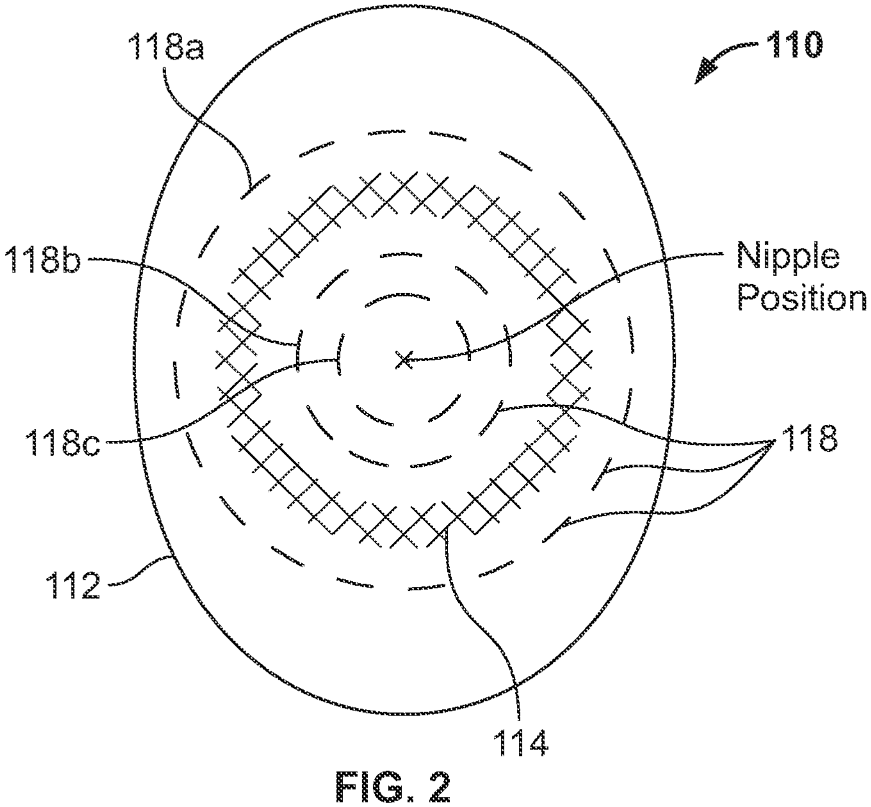
FIG. 2 is another exemplary embodiment of a diversified graft which includes meshing and a plurality of slits arranged in patterns that form regions having different properties.

In an alternate exemplary embodiment shown in FIG. 2, the diversified graft may be a diversified pre-pectoral graft 110 similar to that of FIG. 1 and comprising a main body 112 which comprises an acellular dermal matrix having a generally planar shape (as shown in FIG. 2) prior to implanting and a thickness (not shown per se). In the embodiment shown in FIG. 2, however, the main body 112 of the diversified pre-pectoral graft 110 comprises a first expansion feature, i.e., a plurality of slits 118 which form two or more concentric circular patterns, e.g., three concentric circular patterns 118*a*, 118*b*, 118*c* as shown in FIG. 2, as well as a second expansion feature, i.e., meshing 114, which is arranged in one or more annular patterns. Each of the meshed annular patterns 114 (note that only one annular pattern is shown in FIG. 2) is positioned in between two of the concentric circular patterns 118*a*, 118*b* formed by the plurality of slits 118. In the alternative exemplary embodiment shown in FIG. 2, the regions formed by each of the plurality of slits 118 and meshing 114 are alternating circular or annular regions, rather than upper and lower poles. In some embodiments, such circular regions, annular regions, or both, may be other than concentric (e.g., having their center points offset or staggered compared to one another). In some embodiments, the plurality of slits, the second expansion feature, or both, may form patterns having oval shapes, or some other desired shape, instead of circular or annular.

More particularly, the first region comprising the concentric circular patterns 118*a*, 118*b*, 118*c* which are formed by the plurality of slits 118 has at least one property, such as a first expansion ability, while the second region comprising the annular pattern of meshing 114 (which lies between two of the concentric circles 118*a*, 118*b* of slits 118) also has at least one property, such as a second expansion ability which is different in degree from, i.e., greater than, the first expansion ability provided by the concentric circular patterns 118*a*, 118*b*, 118*c* formed by the plurality of slits 118. The embodiment of the diversified graft 110 shown in FIG. 2 which has an arrangement of different expansion features (i.e., heterogenous features) on the main body 112 thereof, has an overall enhanced, additional expansion ability, while maintaining at least a portion (i.e., not sacrificing all) of the load bearing capability otherwise possessed by a graft which only had a single expansion feature (a plurality of slits 118 arranged in concentric circular patterns 118*a*, 118*b*, 118*c*).

Figure 3:
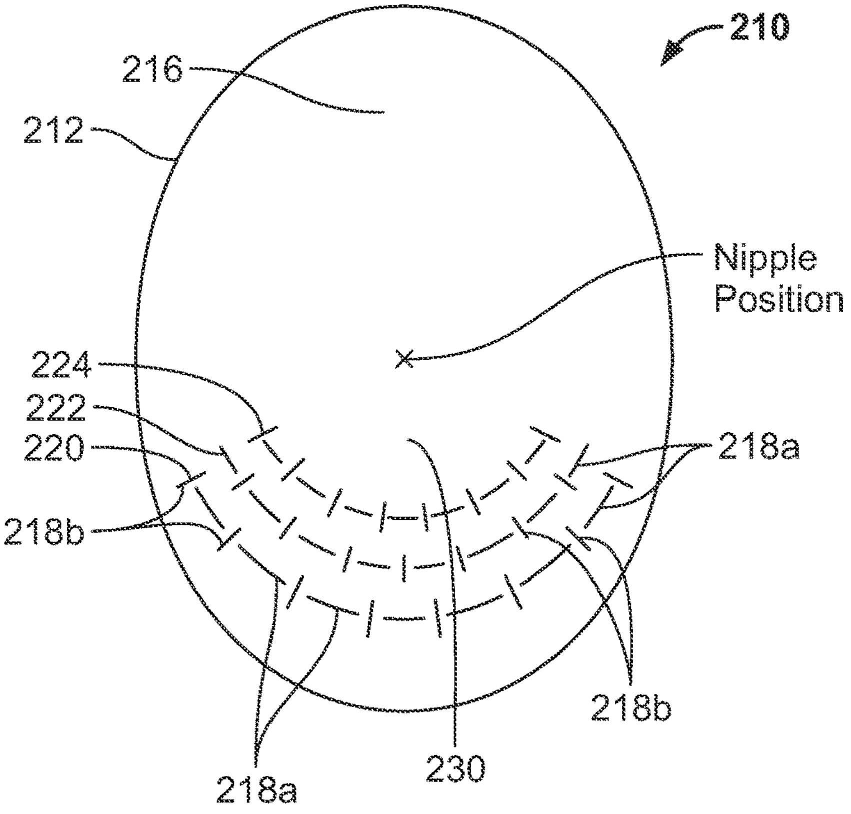
FIG. 3 is another exemplary embodiment of a diversified graft which includes a plurality of slits arranged in a particular patterns to enhance expansion ability of the graft.

In another alternate exemplary embodiment shown in FIG. 3, the diversified graft may be a diversified pre-pectoral graft 210 similar to that of FIG. 1 and comprising a main body 212 which comprises an acellular dermal matrix having a generally planar shape (as shown in FIG. 3) prior to implanting and a thickness (not shown per se). In the embodiment shown in FIG. 3, however, the main body 212 of the diversified pre-pectoral graft 210 comprises a modified expansion feature which comprises a specific arrangement of a plurality of slits 218*a*, 218*b*. More particularly, as shown in FIG. 3, a plurality of slits 218*a*, 218*b* is arranged in two or more concentric arcs, e.g., three concentric arcs 220, 222, 224, as shown in FIG. 3. This modified expansion feature forms a region, such as a lower pole 230, of the main body 212 of the diversified graft 210 that has at least one property comprising an ability for increased expansion of that lower pole region 230 of the main body 212 of the diversified graft 210, while the absence of an expansion feature on the upper pole 216 of the main body 212 leaves that region with a minimized or possibly even absent expansion ability.

With reference to a single exemplary arc 220 of the expansion feature of the diversified graft 210 shown in FIG. 3, each arc (220, 222, 224) comprises an alternating pattern of "horizontal" slits 118*a* which are oriented in line with the curved arc 220 and "vertical" slits 118*b* which are oriented perpendicularly to the midpoint of the arc 220. In adjacent rows, e.g., rows 120, 122, the horizontal and vertical slits 118*a*, 118*b* would also be lined up with each other.

In some embodiments, the diversified graft according to the invention described and contemplated herein comprises a main body having a generally planar shape prior to implanting, the main body comprising at least two components combined or connected with one another and including a first component comprising a first tissue derived matrix, a second component, and, optionally, one or more additional components, wherein the second and one or more additional components are each, independently, selected from: a tissue derived matrix of the same or different type as the first tissue derived matrix, a natural material, or a synthetic material.

Natural materials which are biocompatible and suitable for use in the diversified grafts described and contemplated herein include, without limitation, collagen, elastin, fibrin, cellulose, alginate, silk, cotton, flax, hemp, and the like.

Suitable natural and synthetic materials for use in the diversified grafts described and contemplated herein include, without limitation, natural and synthetic polymers. Suitable synthetic polymers include, but are not limited to, bioabsorbable polymers such as polylactic acid (PLA), polyglycolic acid (PGA), polylactic-coglycolide acid (PLGA), polyglactin 910, and other polyhydroxyacids, polycaprolactones, polycarbonates, polyamides, polyanhydrides, polyamino acids, polyortho esters, polyacetals, degradable polycyanoacrylates and degradable polyurethanes, as well as a polylactide-coglycolide (PLAGA) polymer or a polyethylene glycol-PLAGA copolymer. Examples of natural polymers include, but are not limited to, proteins such as albumin, collagen, elastin, fibrin, hyaluronic acid and its derivatives, naturally occurring polyamino acids, and polysaccharides such as alginate, heparin, and other naturally occurring biodegradable polymers of sugar units. The polymeric blend may also include without limitation polycarbonates, polyfumarates, and caprolactones. The source of natural polymers used with the invention described and contemplated herein is not limited and may, for example without limitation, be mammal- or plant-derived.

The components of the main body of the diversified graft are combined or attached to one another along one or more interfaces therebetween to form the generally planar main body. The components are combined or connected to one another using any suitable connecting means or techniques as are known now or in the future to persons of ordinary skill in the relevant art. For example, the connecting means or techniques include, without limitation, physical means (e.g., sutures, staples, adhesives, melting), chemical means (e.g., crosslinking, polymerizing, etc.), and other suitable and effective biocompatible means and techniques. Combining smaller pieces of tissue derived matrices with other smaller pieces of tissue derived matrices or components made of materials other than tissue derived matrices provides a way to produce larger diversified grafts, thereby making efficient use of more of the tissue samples obtained and minimizing waste.

The shapes and lengths of interfaces of the components which are combined or connected to form the main body of the diversified graft may be the same or different from one another. More particularly, depending on the configuration (i.e., size, shape and dimensions) of each component and the desired overall configuration of the diversified graft to be produced therefrom, each interface may, independently of one another, be linear, curved, annular, curvilinear, irregular, or combinations thereof. In other words, each interface may be, or include a combination of, one or more linear, curved, annular, curvilinear, or irregular segments.

Figure 4:
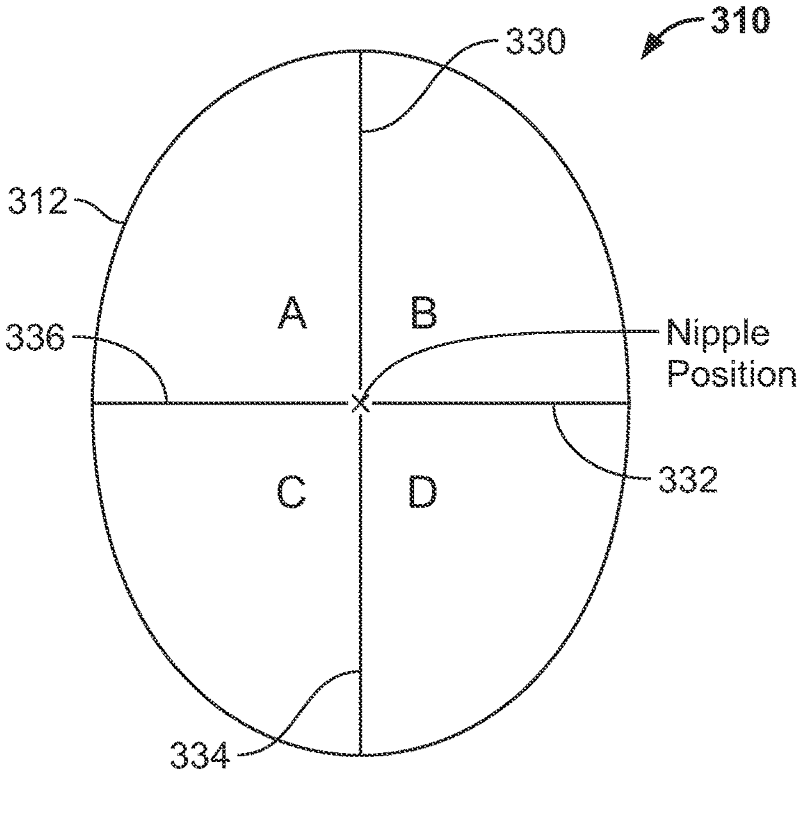
FIG. 4 is still another exemplary embodiment of a diversified graft which comprises multiple smaller components attached to one another to form a larger graft of a more useful size and dimensions.

In still another exemplary embodiment, the main body 312 of a diversified graft 310 may comprise at least two components, e.g., four components A, B, C, D as shown in FIG. 4, at least a first of which (A) comprises a tissue derived matrix, while each of the remaining components (B, C, D) is, independently, selected from: a tissue derived matrix of the same or different type as the first tissue derived matrix, a natural material, or a synthetic material. The simplest embodiment of such a diversified graft 312 is where multiple pieces of the same type of tissue derived matrix, for example without limitation, a matrix derived from the same tissue type and donor source, such as where multiple pieces of an allogenic (human) acellular dermal matrix, are combined or attached to one another along one or more interfaces 330, 332, 334, 336 therebetween to form a larger generally planar main body 312 of the diversified graft 310.

When the diversified graft is produced from components made of two or more different materials, the materials may, for example without limitation, include a combination of allogenic tissue derived matrix and synthetic material, or a combination of an allogenic tissue derived matrix and a xenogenic tissue derived matrix, or a combination of a xenogenic tissue derived matrix and a synthetic material, or two pieces of the same material type. In other words, one or more components A, B, C, D may comprise an allogenic tissue derived matrix, while a different one or more components A, B, C, D may comprise a synthetic material. Alternatively, one or more components A, B, C, D may comprise an allogenic tissue derived matrix, while a different one or more components A, B, C, D may comprise a xenogenic tissue derived matrix.

Figure 5:
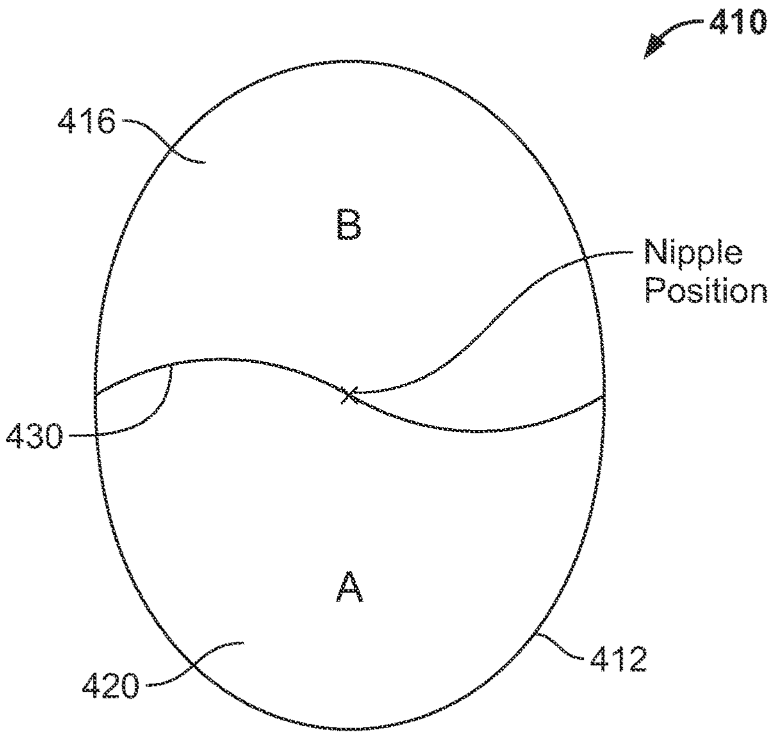
FIG. 5 is another exemplary embodiment of the diversified graft of FIG. 4, but including only two components which are affixed together along a preferred curvilinear interface.

FIG. 5 shows an exemplary embodiment of a diversified pre-pectoral graft 410 for use in pre-pectoral breast reconstruction procedures and comprising a main body 412 which includes a first component A and a second component B which are attached along a curvilinear interface 430. More particularly, the first lower component A forms a lower pole 420 and may comprise a tissue derived matrix, such as without limitation, acellular dermal matrix in the shape of known shaped grafts which are commercially available under the tradename FlexHD® Pliable Shaped from The Musculoskeletal Transplant Foundation located in Edison, New Jersey, United States. The second upper component B forms an upper pole 416 and may, for example without limitation, comprise a synthetic material. It should be noted that any known biocompatible material (e.g., synthetic, allograft, xenograft) may, in fact, be used for either or both of the first and second components A, B. In this embodiment, as will be understood and appreciated by persons of ordinary skill in the relevant art, the upper "peak" of component A should be high large enough such that this upper peak will be sufficient to cover the nipple-areolar complex when used in breast reconstruction procedures. The first and second components A, B may be connected by any suitable and appropriate means and techniques, depending on the types of materials used, as described hereinabove.

Additionally, as will be readily understood by persons of ordinary skill in the relevant art, either or both of the first and second components A, B may be provided with two or more heterogenous features, such as the expansion features described hereinabove, to produce diversified grafts having differentiated upper and lower poles, as also described hereinabove. Furthermore, expansion features of the same type, dimensions, configurations, etc., may also be added to each of the first and second components A, B of the embodiment shown in FIG. 5.

Figure 6:
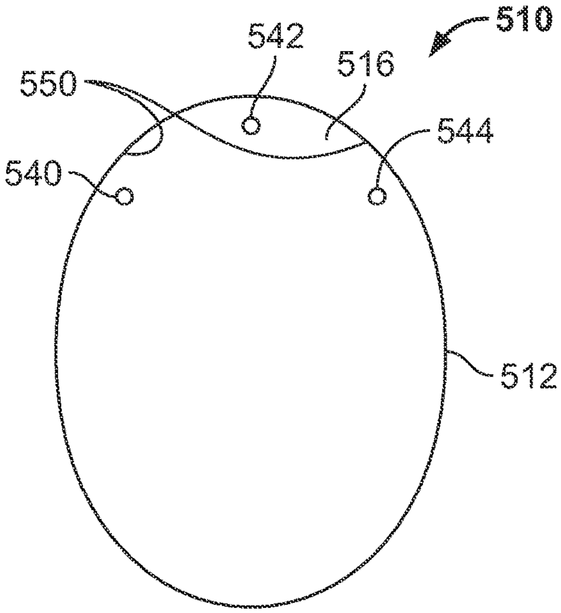
FIG. 6 is a schematic view of a graft having positional suture holes to facilitate positioning and affixing the graft to a patient.

Additional features may be added to the diversified grafts described and contemplated herein to further enhance, facilitate, and improve their use in repair and reconstruction procedures. For instance, with reference to FIG. 6, suture/alignment holes or openings 540, 542, 544 may be added at selected or desired positions on the diversified graft 510. For example, for alignment, the holes 540, 542, 544 may be added at the 10, 12, and 2 o'clock positions on the peripheral edge 550 of the main body 512 to denote the upper portion 516 of the diversified graft 510. Any desired locations or patterns for the holes could be used for this purpose. Additionally, the edges of each hole 540, 542, 544 may be hardened (e.g., via a laser heating, chemical treatment, etc.) to limit tear resistance when a suture (not shown per se) is passed through the holes 540, 542, 544. Such suturing may be employed to affix the diversified graft 510 to the implantation site (not shown), or when a suture (not shown per se) is placed through two or more of the holes 540, 542, 544, the suture could be used to secure the diversified graft 510 around an implant (not shown).

Figure 7:
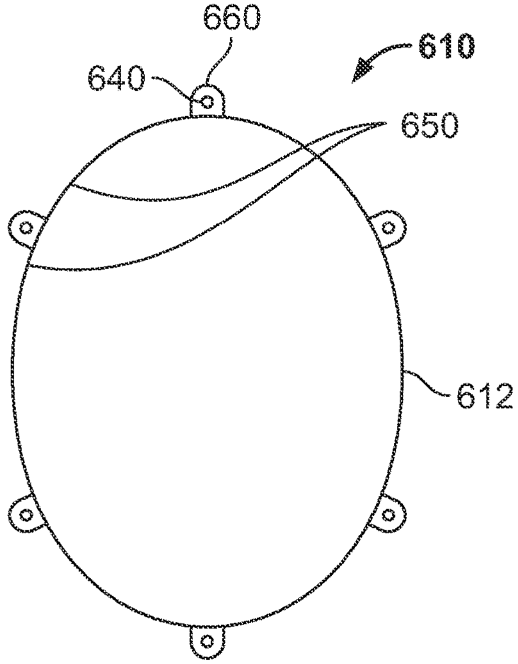
FIG. 7 is a schematic view of a graft having tabs with optional suture holes to facilitate positioning and affixing the graft to a patient.

With reference to FIG. 7, the diversified grafts 610 may further comprise one or more tabs 660 positioned along the peripheral edge 650 of the main body 612 of the diversified graft 610. Such tabs 660 could be useful for attaching a suture (not shown) to the graft 610. Additionally, instead of adding holes to the peripheral edge 650 of the main body 612 of the graft 610, each of tabs 660 could include one or more holes 640, as described above. For example, without limitation, the tabs 660 may be formed at the time of cutting the larger graft 610, or could be separate, discrete tissue pieces which are cut and attached to the peripheral edge 650 of the main body 612 of the graft 610 in a manner as described above in connection with the embodiments of FIGS. 4 and 5 wherein attaching two or more components together to form the diversified grafts 310, 410, respectively, was explained. Of course, any one or more features for aligning or attaching, or both, a diversified graft at an implant site, such as without limitation, tabs, straps, holes, pre-attached sutures, notches, markings, indicia, etc., may be provided on virtually any embodiment of the diversified grafts described and contemplated herein.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

We claim:

1. A graft useful in surgical repair and reconstruction procedures which treat a body feature of a subject, the graft comprising:

a main body which comprises:

a first component comprising a first material which comprises a first tissue derived matrix produced from one or more tissue samples, and a second component comprising a second material which is different from the first material, the second material comprising either or both of at least one synthetic material, or a second tissue derived matrix produced from one or more tissue samples and which includes a second tissue type different from the first tissue derived matrix, wherein the first and second components are combined, connected, or attached with one another, and partially overlap one another to form the main body; and two or more heterogenous features each of which forms a region of the main body, each region having a physical property which is different from a physical property of at least one other region, wherein the main body of the graft has a first region having a first heterogenous feature, and a second region having a second heterogenous feature which is different from the first heterogenous feature, wherein the second component has a size and shape which is substantially coextensive with the main body, the first component is smaller than the second component and is combined with and overlaps a portion of the second component, wherein the main body has a layered portion comprising the first tissue derived matrix of the first component and the second material of the second component and an unlayered portion which lacks the first tissue derived matrix, and wherein the layered portion of the main body includes the first region and the first heterogenous feature and the unlayered portion of the main body includes the second region and the second heterogenous feature.

2. The graft of claim 1, wherein the main body has a generally planar shape prior to implanting, and wherein, during and after implanting in, on, or proximate to, the body feature, the graft reconfigures from the generally planar shape to a three-dimensional shape which conforms to the size, shape, or both, of the body feature being treated, or a portion thereof.

3. The graft of claim 1, wherein the first tissue derived matrix comprises a tissue type selected from: dermal, adipose, submucosal, fascia, other planar tissue types, and combinations thereof.

4. The graft of claim 1, wherein the tissue type of the second tissue derived matrix is selected from: dermal, adipose, submucosal, fascia, other planar tissue types, and combinations thereof.

5. The graft of claim 1, wherein the types of heterogenous features include: expansion features, lack of expansion features, thickness, fluid egress features, type of material, degree of decellularization, cell viability, degree of delipidation, and degree of crosslinking.

6. The graft of claim 1, wherein the physical property is selected from: flexibility, stiffness, elasticity, tensile strength, ductility, mechanical strength, weight capacity, load-bearing capacity, expansion capacity, coverage area, density, compression resistance, suture retention, tear resistance, or combinations thereof.

7. The graft of claim 1, wherein the body feature being treated by the surgical repair and reconstruction procedure is a breast having a lower pole and an upper pole, and wherein the first region of the main body is a lower pole region and the first heterogenous feature comprises either the absence of expansion features, or a plurality of cuts or slots, at least some of which extend or pass through a portion of, or the entire, thickness of the main body, and wherein the second region of the main body is an upper pole region, and the second heterogenous feature comprises meshing.

8. The graft of claim 7, wherein the second component comprises a biocompatible synthetic material.

9. The graft of claim 7, wherein the main body has a generally planar shape prior to implanting, and wherein, when the graft is implanted, the lower pole region of the main body at least partially aligns with the lower pole of the breast being treated and the upper pole region of the main body at least partially aligns with the upper pole of the breast being treated.

10. The graft of claim 1, wherein the body feature being treated by the surgical repair and reconstruction procedure is a breast having a lower pole and an upper pole, and wherein the first region of the layered portion of the main body is a lower pole region and the first heterogenous feature comprises either the absence of expansion features, or a plurality of cuts or slots, at least some of which extend or pass through a portion of, or the entire, thickness of the main body, and wherein the second region of the unlayered portion of the main body is an upper pole region, and the second heterogenous feature comprises meshing.

11. The graft of claim 10, wherein the second component comprises a biocompatible synthetic material.

12. The graft of claim 10, wherein the main body has a generally planar shape prior to implanting, and wherein, when the graft is implanted, the lower pole region of the main body at least partially aligns with the lower pole of the breast being treated and the upper pole region of the main body at least partially aligns with the upper pole of the breast being treated.

13. The graft of claim 1, wherein the body feature being treated by the surgical repair and reconstruction procedure is a breast having a lower pole and an upper pole, and wherein the first region of the main body is a lower pole region and the first heterogenous feature comprises meshing and wherein the second region of the main body is an upper pole region, and the second heterogenous feature comprises either the absence of expansion features, or a plurality of cuts or slots, at least some of which extend or pass through a portion of, or the entire, thickness of the main body.

14. A graft useful in surgical repair and reconstruction procedures which treat a body feature of a subject, the body feature comprising breast having a lower pole and an upper pole, the graft comprising:

a main body which comprises:

a first component comprising a first material which comprises a first tissue derived matrix produced from one or more tissue samples, and a second component comprising a second material which is different from the first material, the second material comprising a biocompatible synthetic material and, optionally, also a second tissue derived matrix produced from one or more tissue samples and which includes a tissue type different from the first tissue derived matrix, wherein the first and second components are combined, connected, or attached with one another to form the main body; and two or more heterogenous features each of which forms a region of the main body, each region having a physical property which is different from a physical property of at least one other region, wherein the main body of the graft has a first region having a first heterogenous feature, and a second region having a second heterogenous feature which is different from the first heterogenous feature, wherein each of the first component and the second component has a size and shape which is substantially coextensive with the main body, the first and second components being substantially aligned, overlapping, and layered together, wherein the main body is layered, and wherein the first region of the main body is a lower pole region and the first heterogenous feature comprises either the absence of expansion features, or a plurality of cuts or slots, at least some of which extend or pass through a portion of, or the entire, thickness of the main body, and wherein the second region of the main body is an upper pole region, and the second heterogenous feature comprises meshing.

15. The graft of claim 14, wherein the main body has a generally planar shape prior to implanting, and wherein, when the graft is implanted, the lower pole region of the main body at least partially aligns with the lower pole of the breast being treated and the upper pole region of the main body at least partially aligns with the upper pole of the breast being treated.

16. The graft of claim 14, wherein the tissue type of the first tissue derived matrix is selected from: dermal, adipose, submucosal, fascia, other planar tissue types, and combinations thereof.

17. The graft of claim 14, wherein the tissue type of the second tissue derived matrix is selected from: dermal, adipose, submucosal, fascia, other planar tissue types, and combinations thereof.

18. The graft of claim 14, wherein the main body further comprises a third heterogenous feature which forms a third region of the main body a physical property which is different from a physical property of at least one other region, wherein the third heterogenous feature includes one or more of: expansion features, lack of expansion features, thickness, fluid egress features, type of material, degree of decellularization, cell viability, degree of delipidation, and degree of crosslinking.

* * * * *